United States Patent [19]
Kalshoven

[11] Patent Number: 5,914,779
[45] Date of Patent: Jun. 22, 1999

[54] PORTABLE FLASH LAMP REFLECTANCE ANALYZER SYSTEM AND METHOD

[75] Inventor: James Edward Kalshoven, Seabrook, Md.

[73] Assignee: The United States of America as represented by the Administrator of the National Aeronautics and Space Administration, Washington, D.C.

[21] Appl. No.: 08/946,062

[22] Filed: Oct. 7, 1997

[51] Int. Cl.[6] .................................................... G01N 21/64
[52] U.S. Cl. ........................................ 356/317; 250/458.1
[58] Field of Search ................................... 350/326, 328, 350/317, 318, 417; 250/458.1, 459.1, 461.1, 461.2

[56] References Cited

U.S. PATENT DOCUMENTS 3,836,782  9/1974  Forbes et al. ......................... 250/461.1
4,200,801  4/1980  Schuresko ............................ 250/458.1

OTHER PUBLICATIONS

James E. Kalshoven and David P. Rosten, "An Active Optical Remote Sensing System for Vegetation Index Determination", IEEE International Geoscience and Remote Sensing Symposium Remote Sensing for a Sustainable Future, IEEE Catalog No. 96CH35875, vol. III, pp. 1809–1811, USA, May 27–31, 1996.

James E. Kalshoven, Airborne Ground Illuminator for Hyperspectral Validation and Calibration, SPIE Proceedings Earth Observing System, vol. 2820, pp. 67–71, USA, Aug. 5–6, 1996.

*Primary Examiner*—F. L. Evans

[57] ABSTRACT

The system and method allow spectroscopic analysis of vegetation or the like without effects from changing sun and cloud conditions, undesired portions of the area of interest or atmospheric disturbances. The system (1) includes a light source (5) such as a xenon flash lamp, a telescope (7), a spectrometer (9), an analog/digital converter (11), a memory (13), a display (15), and an on-board microprocessor (17) or a port (19) for attachment to a laptop computer. The system is taken to an area of interest in the woods (step 41), the vegetation is illuminated from below (step 43) and data are taken (step 45).

9 Claims, 2 Drawing Sheets

PORTABLE FLASH LAMP REFLECTANCE ANALYZER SYSTEM AND METHOD

ORIGIN OF THE INVENTION

The invention described herein was made by an employee of the United States Government, and may be manufactured and used by or for the Government for governmental purposes without the payment of any royalties thereon or therefor.

TECHNICAL FIELD

The invention is directed to a system and method for the study of a scene containing objects such as vegetation or the like by spectral analysis of reflected light.

BACKGROUND ART

The most common method for determining the most popular plant parameters is to use a specially configured, hand-held light detector sensitive to the sun. The user carries such a hand-held device through a forest after having gathered reference data in a clear-to-the-sky field, and the solar radiation transmitted through the canopy is recorded.

One disadvantage of such a method comes in separating effects generated by leaves from effects generated by branches, since both leaves and branches block light. Moreover, changing sun and cloud conditions limit the time in which valid data can be taken before it becomes necessary to take new reference data in the clear-to the sky field.

Aircraft-based instruments using the sun have been used to study vegetation; however, such instruments have atmospheric and sun angle effects to confuse the results. The present inventor has used an aircraft-based detector with a flash lamp to take data, but the backscatter from the earth's surface convolves both soil and leaf undercover and living plant characteristics. The present inventor's experiences with aircraft-based detectors are described in the papers "An Active Optical Remote Sensing System for Vegetation Index Determination" by J. E. Kalshoven, et al and "Airborne Ground Illuminator for Hyperspectral Validation and Calibration" by J. E. Kalshoven, presented at conferences of the IEEE and SPIE, respectively, in July, 1996. Both of these papers are hereby incorporated by reference in their entireties into the present disclosure.

Fluorescence-based systems use lasers to excite a surface. Such systems must be custom-designed for specific applications in laboratory settings.

STATEMENT OF THE INVENTION

It is an object of the invention to provide a system and method for spectroscopic analysis of a scene containing objects such as vegetation or the like with reduced dependence on sun and cloud conditions, atmospheric effects, sun angle effects and backscatter from the earth's surface.

It is a further object of the invention to provide such a system and method which, when used with vegetation, allow the taking of data from leaves with reduced interference from branches.

It is a further object of the invention to provide such a system and method which allow the use of portable equipment and which do not have to be custom-designed for any specific application.

To achieve these and other objects, the invention is directed to a system including a flash lamp and a spectrometer, with appropriate optics, configured in a coaxial manner which allows the spectrometer to view the scene illuminated by a flash from the flash lamp and collect the backscattered light energy. The system is compact so it can be taken conveniently out of a laboratory and used in a field or forest. A linear array of detectors is used at the output of the spectrometer. The light, before falling on these detectors, is spread out or dispersed by the spectrometer optics in a manner dependent on the parameters set for the spectrometer and desirable for the output needed. Once the system is manufactured, it is useful to calibrate the spectrometer so that the spectrometer optics and the linear array are in correct positions relative to each other to allow the taking of valid data. For example, a manufacturing defect may cause light of a certain wavelength to fall on a photo-detector other than the one intended to detect that wavelength, in which case the data taken will be invalid; in such a case, correction is necessary. Of course, the wavelength range that the system can detect should correspond to the wavelength range of interest in the intended use. Many or few wavelengths can be incident on each detector in the array, the total being a continuous spectrum over a selectable wavelength range. Spectral blocking filters can also be used in front of the flash lamp, and induced fluorescence can also be sought at various non-filtered wavelengths in the backscattered light. The system has built in electronics or can be computer controlled, for data acquisition and for calibration using a reference target of known spectral reflectance characteristics. The spectral output, which is the basic data product of the system according to the present invention, allows users to more precisely apply spectroscopic operations developed by scientists based on the reflectance characteristics of plants, water and soil. It will also aid in developing new spectroscopic operations and enhancing existing ones in fields as diverse as agriculture and forestry. These operations can be incorporated into systems according to the present invention for a more advanced data output.

BRIEF DESCRIPTION OF THE DRAWINGS

A preferred embodiment of the invention will now be described in detail with reference to the drawings, in which.

DETAILED DESCRIPTION OF THE INVENTION

Figure 1:
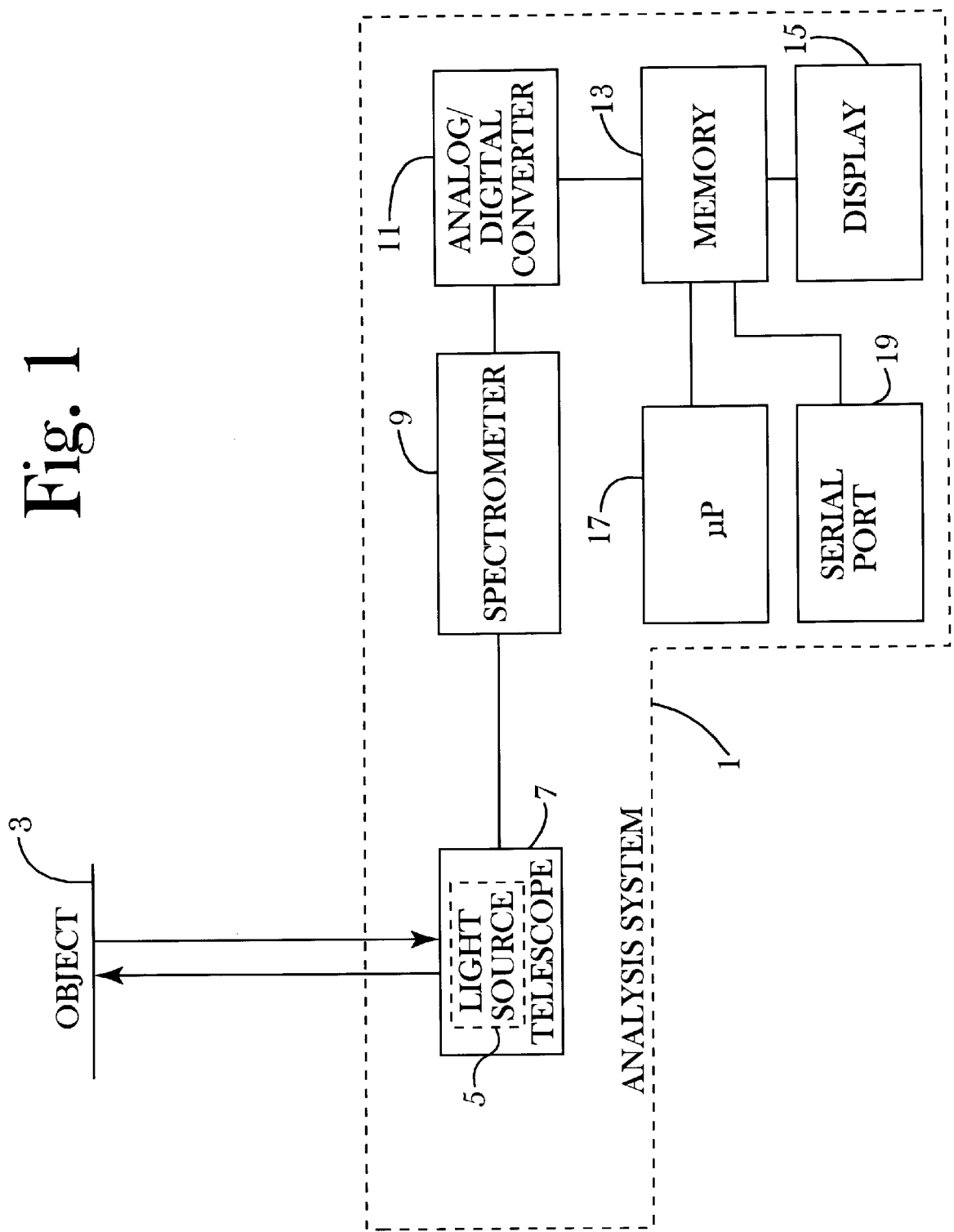
FIG. 1 shows a block diagram of the system according to a preferred embodiment of the present invention.

A system according to the preferred embodiment is shown in FIG. 1. System 1, used to take data from object 3, includes flash lamp or other light source 5, such as a xenon lamp or a photographer's flash gun, mounted next to telescope 7 which receives the reflected light from the flashes off of the surface of object 3. Light source 5 and telescope 7 are located very close together and are preferably coaxial. Such an arrangement avoids shadows. The light from telescope 7 is sent through spectrometer 9 where it is spread out spectrally onto the surface of a linear detector array, such as a CCD array. The field of view is variable if desired. The output of the array is fed to analog/digital converter 11, and the spectral information is either stored in memory 13, displayed on display 15 or both. The data can be analyzed either by dedicated microprocessor 17 or by a laptop computer connected by way of a port (such as serial port 19, a parallel port, or a PCMCIA slot).

Figure 2:
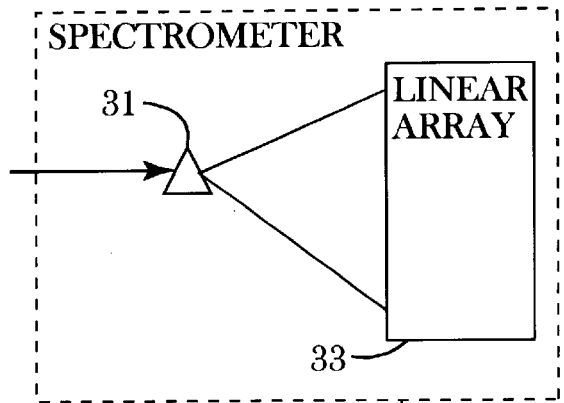
FIG. 2 shows details of a spectrometer used in the system of FIG. 1.

Spectrometer 9 is shown in greater detail in FIG. 2. Light entering spectrometer 9 is made incident on dispersing optical element 31, which may be a prism, a diffraction grating, a holographic optical element or any other suitable element. The light dispersed by dispersing optical element 31 is made incident on linear detector array 33, which, as noted above, may be a CCD array.

Figure 3:
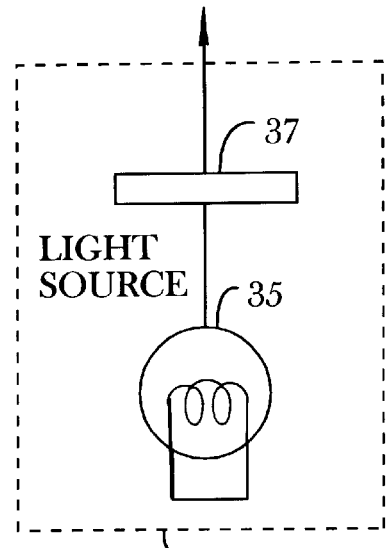
FIG. 3 shows details of a light source used in the system of FIG. 1.

Light source 5 is shown in greater detail in FIG. 3. Light source 5 includes lamp 35 such as a xenon flash lamp and optionally also includes spectral filter 37 for fluorescence data acquisition.

Figure 4:
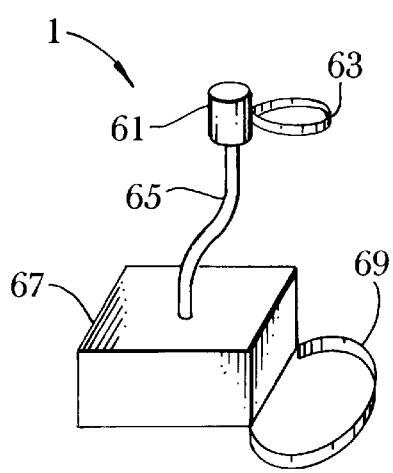
FIG. 4 shows an external view of the system according to the preferred embodiment.

An external view of the system is shown in FIG. 4. Hand-held portion 61 has a band strap 63 and is connected via cable 65 to main portion 67, which has a waist strap 69 for attachment to the user's waist. Hand-held portion 61 contains a light source 5 and telescope 7. Hand-held portion 61 may also contain a spectrometer 9, in which case cable 65 is an electrical cable; alternatively, spectrometer 9 may be in main portion 67, in which case cable 65 is a fiber optic cable. Either way, the system should take up no more than one cubic foot.

Figure 5:
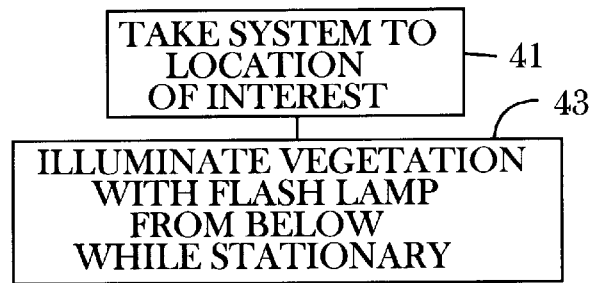
FIG. 5 shows a flow chart of a method of using the system of FIG. 1.

The use of system 1 will now be explained with reference to the flow charts of FIGS. 5 and 6. In step 41, the user carries the system to a location of interest, such as a particular location in a forest. In step 43, the user illuminates the area of interest, such as the vegetation to be analyzed, preferably while holding the system stationary. The illumination is done preferably from below, thus avoiding effects from the ground. In step 45, the data are taken from the reflected light.

Figure 6:
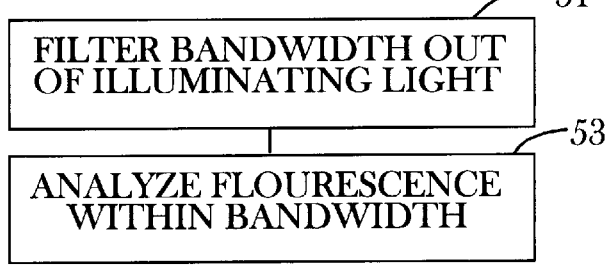
FIG. 6 shows a flow chart of steps used in a modified method of using the system of FIG. 1.

FIG. 6 shows steps in a modification used for studying fluorescence effects of the vegetation. In step 51, a bandwidth is filtered out of the illuminating light by means of filter 37 or the like. In step 53, fluorescence is analyzed within that bandwidth. Thus, the effects observed are known to be caused by fluorescence rather than simply by reflection.

While a preferred embodiment of the present invention has been set forth, it will be readily apparent to those skilled in the art who have studied this specification that the system and method may be modified without departing from the present invention. For example, as part of the analysis, ratios of different parts of the spectrum may be taken in a prescribed manner, according to operations known in the scientific literature. Also, the system could be used with a global positioning system. Therefore, the present invention should be construed as limited only by the appended claims.

I claim:

1. A method of using a system for spectroscopic analysis of an object of interest, the system comprising:

illuminating means for emitting light in at least an upward direction for illuminating the object of interest;

telescope means for receiving a portion of the light which is reflected from the object of interest; and spectrometry means for spectroscopically analyzing the portion of the light which is received by the telescope means to perform the spectral analysis of the object of interest, the method comprising:

(a) transporting the system to a location adjacent to the object of interest;

(b) illuminating the object of interest at least from below with the illuminating means;

(c) receiving the portion of the light reflected by the object of interest with the telescope means; and (d) performing the spectral analysis with the spectroscopy means in accordance with the portion of the light.

2. A method as in claim 1 wherein the location is substantially below the object of interest.

3. A method as in claim 1, wherein the object of interest comprises living vegetation.

4. A method as in claim 1, wherein step (b) comprises equipping the illuminating means with a spectral filter which removes a bandwidth so that the light used to illuminate the object of interest is spectrally filtered.

5. A method as in claim 4, wherein step (d) comprises performing the spectral analysis on wavelengths of the portion of the light within the bandwidth to analyze fluorescence in the object of interest.

6. A method as in claim 1, wherein the system is held stationary during step (b).

7. A system for spectroscopic analysis of an object of interest, the system comprising:

illuminating means for emitting light in at least an upward direction for illuminating the object of interest at least from below;

telescope means for receiving a portion of the light which is reflected from the object of interest; and spectrometry means for spectroscopically analyzing the portion of the light which is received by the telescope means wherein said illuminating means, telescope means, and spectrometry means are located within a housing comprising a hand-held portion and a main portion, these portions being connected to each other via a cable.

8. A system as in claim 7 wherein the hand-held portion houses the illuminating means and the telescope means, the main portion houses the a spectrometry means, and the cable connecting them is a fiber optic cable.

9. A system as in claim 7 use in which the hand-held portion houses the illuminating means, the telescoping means, and the spectrometry means.

* * * * *